United States Patent
Boudet et al.

(10) Patent No.: US 6,509,567 B2
(45) Date of Patent: Jan. 21, 2003

(54) METHOD AND APPARATUS FOR DETECTING GASES

(75) Inventors: Thierry Boudet, Echirolles (FR); Jérôme Fantini, Arras (FR); Emelian Gamarts, St Petersburg (RU); Vladimir Krylov, St Petersburg (RU)

(73) Assignees: Gaz de France, Paris (FR); Oldham France S.A., Arras (FR)

( * ) Notice: Subject to any disclaimer, the term of this patent is extended or adjusted under 35 U.S.C. 154(b) by 33 days.

(21) Appl. No.: 09/866,872

(22) Filed: May 30, 2001

(65) Prior Publication Data

US 2002/0050567 A1 May 2, 2002

(30) Foreign Application Priority Data

May 30, 2000 (FR) .............................. 00 06893

(51) Int. Cl.[7] .............................................. G01N 21/59
(52) U.S. Cl. ..................... 250/345; 250/343; 250/575
(58) Field of Search ................................. 250/343, 344, 250/345, 346, 575; 356/436, 437

(56) References Cited

U.S. PATENT DOCUMENTS

| | | | |
|---|---|---|---|
| 4,053,236 A | 10/1977 | Atwood et al. | 356/189 |
| 4,176,963 A | 12/1979 | Fabinski et al. | 356/418 |
| 4,567,366 A | 1/1986 | Shinohara | 250/339 |
| 4,899,053 A | 2/1990 | Lai et al. | 250/343 |
| 4,914,719 A | 4/1990 | Conlon et al. | 250/339 |
| 5,468,961 A | * 11/1995 | Gradon et al. | 250/343 |
| 5,705,813 A | 1/1998 | Ronge et al. | 250/345 |

FOREIGN PATENT DOCUMENTS

FR  2772127  6/1999

OTHER PUBLICATIONS

P.T. Moseley, J.O.W. Norris and D.E. Williams, "Techniques and Mechanisms in Gas Sensing," pp. 249–255, published by Adam Hilger, Bristol, Philadelphia and New York (Published in 1991, T.M.).

* cited by examiner

Primary Examiner—Constantine Hannaher
Assistant Examiner—Timothy J. Moran
(74) Attorney, Agent, or Firm—McDermott, Will & Emery

(57) ABSTRACT

The apparatus for detecting the presence of a particular gas within a mixture of gases comprises first and second emitter means for emitting measurement and reference electromagnetic radiation beams respectively, which beams are activated in alternation, a measurement cell, a filter cell, first and second detector means for detecting electromagnetic radiation beams, a beam splitter, and acquisition and processing means for synchronously acquiring and processing the four signals $U_S^1$, $U_S^2$, $U_R^1$, $U_R^2$ delivered by the first and second detector means in succession when the first and second emitter means are respectively activated so as to determine the absolute concentration of the gas to be detected on the basis of the ratio $R=(U_S^1 \times U_R^2)/(U_S^2 \times U_R^1)$ between the four signals, in which $U_S^1$ and $U_S^2$ respectively represent the signals delivered by the first and second detector means when the first emitter means is activated, and $U_R^1$ and $U_R^2$ respectively represent the signals delivered by the first and second detector means when the second emitter means is activated.

20 Claims, 4 Drawing Sheets

METHOD AND APPARATUS FOR DETECTING GASES

The present invention relates to a method and to portable apparatus for detecting gas by selective absorption of electromagnetic radiation to detect the presence of a particular gas within a mixture of gases.

BACKGROUND OF THE INVENTION

Gas leak detectors are characterized by three properties, namely: selectivity, i.e. the ability to detect a particular gas amongst a mixture of gases present in an atmosphere; sensitivity, i.e. the minimum quantity of gas that can be detected; and stability, i.e. insensitivity to variations in climatic conditions so as to ensure that performance remains constant regardless of climatic conditions.

Various types of detector are already known for detecting a particular gas, such as methane, in an atmosphere made up of a mixture of gases.

Thus, semiconductor detectors exist in which a combustible gas reacts on coming into contact with the semiconductor, thereby reversibly altering the electrical resistance of the semiconductor, and this resistance is very easy to measure. That type of sensor is of low cost and is used above all for detecting leaks in the home. It has medium performance and stability, but no selectivity.

Catalytic detectors can be used for detecting the presence, e.g. of methane, and they are fitted to detector appliances for detecting methane at concentrations in a measurement range of several hundred parts per million (ppm) to several percent, by volume. Although such detectors have acceptable stability, their selectivity is very poor.

Thermal conductivity detectors use the ability of a gas to evacuate heat. The presence of a gas such as methane gives rise to a variation in thermal conductivity, and this variation is measured. Such appliances are not selective and they are not adapted to measuring low concentrations of gas, e.g. less than 1% by volume of methane.

Flame ionization appliances make use of the fact that hydrocarbon flames conduct electricity. The presence of a hydrocarbon such as methane modifies the conductivity of a hydrogen flame between two electrodes. Sensitivity is good and response times are short. Thus, appliances of that type can be used to measure in the range 1 ppm to several hundred ppm with good stability. However selectivity is zero.

Known infrared optical detectors present medium performance in terms of sensitivity and selectivity.

Various types of non-dispersive infrared (NDIR) type gas detectors are known. Nevertheless, most gas analyzers using standard NDIR type techniques lose their effectiveness when the gases to be detected and measured present absorption bands that are non-specific and overlap in the infrared range.

FIGS. 3 and 3A are diagrams showing an example of an optical type gas analyzer as described in U.S. Pat. No. 4,914,719.

In such an embodiment, a source 10 of infrared radiation powered with alternating current (AC) produces a beam of infrared radiation which passes through a chamber 14 containing a sample of a gas mixture, and it impinges on a beam splitter 12. The beam splitter 12 directs a fraction of the incident radiation to a wheel 16 carrying filters, and the fraction of the infrared radiation which passes through the wheel 16 carrying filters 22, 24, and 26 is picked up by a photodetector 20.

A stepper motor 18 rotates the wheel 16 so as to position the various filters 22, 24, and 26 in turn between the beam splitter 12 and the detector 20.

The fraction of the infrared radiation that passes through the beam splitter 12 passes initially through an interference filter 30 and is then picked up by a photodetector 28.

FIG. 4 shows typical curves representing the transmission spectrum as a function of wavelength for three gases A, B, and C having absorption bands that overlap. It can be observed that a standard NDIR type gas detection technique using a bandpass filter centered on wavelength $\lambda$ and presenting a half-maximum bandwidth $\Delta\lambda$, as shaded in FIG. 4 is incapable of distinguishing between the three gases A, B, and C insofar as all three gases A, B, and C present various absorption bands in this zone of the spectrum. Insofar as a standard technique makes it possible to perform a transmission measurement only, it is possible to obtain only one equation having three unknowns (three gas concentrations).

The apparatus shown in FIGS. 3 and 3A enables this problem to be remedied by placing three bandpass filters 22, 24, and 26 on the wheel 16, the filters having narrow bands centered on wavelengths $\lambda_1$, $\lambda_2$, and $\lambda_3$, with respective bandwidths $\Delta\lambda_1$, $\Delta\lambda_2$, and $\Delta\lambda_3$ thus enabling a set of three equations to be obtained. Under such circumstances, the filter 30 is itself connected in such a manner as to correspond to a reference beam centered on the wavelength $\lambda_0$ which is close to the characteristic absorption wavelength of the gases present in the chamber 14, but which does not overlap these characteristic absorption wavelengths.

The prior art apparatus of FIGS. 3 and 3A thus provides a set of four measurement signals that can be used to detect the concentration of three different gases. The apparatus can be adapted to detecting the concentrations of N different gases providing N filters 22, 24, and 26 are selected that are centered on different wavelengths.

Although such an apparatus as known from U.S. Pat. No. 4,917,719 enables a plurality of gases to be detected simultaneously, it is not adapted to detecting a particular gas simply and quickly using a portable appliance. The apparatus described above with reference to FIGS. 3 and 3A has moving parts, in particular the rotary disk 16, which increases the weight and the size of the apparatus and also the amount of energy it consumes, while also making the apparatus relatively fragile, particularly in the presence of vibration. Furthermore, such apparatus can be used only on condition that the composition of the gas mixture for analysis is known in advance, and it needs to be calibrated for each gas whose concentration is to be determined within the mixture of gases.

Other types of NDIR gas analyzer are known, that implement a gas filter correlation (GFC) technique. By way of example, such gas analyzers are described in the work entitled "Techniques and mechanisms in gas sensing" by P. T. Moseley, J. O. W. Norris, and D. E. Williams, published by Adam Hilger, Bristol, Philadelphia, and New York.

In that technique, the gas to be measured is used in high concentration as a filter for the infrared radiation passing through the chamber of the gas analyzer that is filled with the gas mixture to be analyzed. The basic components of a gas analyzer using the GFC technique and designed to measure ambient carbon monoxide CO are shown in FIG. 5.

The infrared radiation emitted by a source 40 is chopped and then passes through a gas filter which comprises in alternation a reference filter 42 containing a high concentration of a gas of the same kind as that which is to be detected in the mixture of gases (such as carbon monoxide), and a measurement gas filter 43 containing nitrogen in this example. The gas filters 42 and 43 pass in alternation in front of the source 40, given that they are placed on a support which is rotated by a motor 41 defining the chopping of the beam from the source 40. Once the beam of radiation has passed through the gas filter device 42, 43 it can pass through an additional bandpass filter 44 and then penetrates into a chamber 45 containing the mixture of gases and within which absorption occurs due to the gases in the mixture of gases. Once the infrared beam has passed through the chamber 45 it reaches a photodetector 47, after passing through a lens system 46 that performs focusing and that also contains an interference filter having a narrow passband. The detector 46 is associated with electronic processor circuits 48 and with a display device 49.

If the chamber 45 does not contain a gas that causes infrared radiation to be absorbed and if the radiation from the source $\lambda_0$ passes through the CO filter 42, then the spectrum of the light intensity received by the detector 47 as a function of wavelength has the form shown in FIG. 6A. The dashed line envelope of the curve is due to the presence of the narrow band filter, while the notches are due to individual spectrum lines in the absorption spectrum of CO. The shaded zone corresponds to the total energy contained in the beam. The CO filter has eliminated all of the radiation that could be absorbed by CO such that the CO present in the chamber 45 cannot further reduce the energy in the beam. Nevertheless, other gases present in the chamber 45 and having absorption spectra that overlap that of CO can absorb energy from the infrared beam. The CO filter 42 serves to produce a reference beam.

In contrast, when the infrared beam passes through the nitrogen filter 43, no energy is absorbed by the nitrogen, and in the absence of any absorbent gas in the chamber 45, the spectrum of the signal reaching the detector 47 is in the form shown by dashed lines in FIG. 6B, which form is due to the presence of a bandpass filter. The measurement beam that has passed through the nitrogen filter 43 and the reference beam that has passed through the carbon monoxide filter 42 can be brought into equilibrium by means of a neutral density filter, for example. When the chamber 45 does not contain any absorbent gas, the balanced energies of the beams that have passed through the filters 42 and 43 lead to a zero difference signal being detected.

In the event of the chamber 45 containing a mixture of gases that include carbon monoxide, the carbon monoxide cannot absorb radiation in the reference beam but can absorb radiation in the measurement beam, thereby leading to spectra shown respectively in FIGS. 6C and 6D. The energy difference between the reference beam and the measurement beam leaving the chamber 45 leads to an output signal being issued that represents the concentration of CO in the chamber 45.

Absorption by an interfering gas present in the measurement cell 45 causes the apparatus of FIG. 5 to give a positive output signal for the regions of the spectrum of the interfering gas where there is overlap with the absorption lines of CO, and its gives a negative signal for regions of the spectrum of the interfering gas where there is no overlap with the absorption lines of CO.

Thus, in the presence of an interfering gas, there exists a weak residual output signal whose sign and amplitude depend on the sample and on the overlap of the absorption spectra of the gas to be measured (CO) and of the interfering gas.

It can be seen that a measurement technique of the kind set out in the above-specified work provides more effective elimination of the influence of interfering gases than do the apparatuses described in U.S. Pat. No. 4,914,719, and, in addition, does not require calibration for each specific gas.

Nevertheless, the apparatuses described in the above-cited work also make use of moving parts such as the rotary wheel supporting the gas cells that form filters, and such apparatuses cannot be implemented in a form that is simultaneously compact, robust, and not greedy for energy.

OBJECTS AND SUMMARY OF THE INVENTION

The present invention seeks to remedy the above-specified drawbacks and to enable gas detectors to be made that present simultaneously: excellent sensitivity to a predetermined gas; good selectivity relative to said predetermined gas; good robustness against shocks; low weight; and small size, enabling it to be implemented in portable form and at low cost, while not requiring any special maintenance.

The invention also seeks to provide a gas detector that has good stability against temperature variations.

These objects are achieved by a portable apparatus for detecting gas by selective absorption of electromagnetic radiation to detect the presence of a particular gas in a gas mixture, the apparatus comprising:

a) first emitter means for emitting a measurement infrared electromagnetic radiation beam in a wavelength band containing a wavelength at which the gas to be detected presents an absorption characteristic;

b) second emitter means for emitting a reference infrared electromagnetic radiation beam, said first and second emitter means being activated in alternation;

c) a measurement cell containing the gas mixture to be analyzed, which measurement cell has an inlet section and an outlet section and receives at least a fraction of the measurement beam through its inlet section;

d) a filter cell containing a sample of the gas to be detected and having an inlet section and an outlet section, through which sections at least a fraction of the reference beam passes in succession;

e) first detector means for detecting electromagnetic radiation beams;

f) second detector means for detecting electromagnetic radiation beams;

g) a beam splitter disposed in such a manner as to split firstly the measurement beam and secondly the reference beam so as to transmit a first fraction of each of the measurement and reference beams to said first detector means, and a second fraction of each of the measurement and reference beams to the second detector means; and h) processing and acquisition means for synchronously acquiring and processing the four signals ($U_S^1$, $U_S^2$, $U_R^1$, $U_R^2$) delivered by the first and second detector means in succession when the first and second emitter means are respectively activated in order to determine the absolute concentration of the gas to be detected on the basis of the ratio $R=(U_S^1 \times U_R^2) \div (U_S^2 \times U_R^1)$ between said four signals where $U_S^1$ and $U_S^2$ respectively represent the signals delivered by the first and second detector means when the first emitter means is activated, and where $U_R^1$ and $U_R^2$ respectively represent the signals delivered by the first and second detector means when the second emitter means is activated.

In a first embodiment, the filter cell containing a sample of gas to be detected has inlet and outlet sections through which the entire reference beam passes in succession; the beam splitter is placed in such a manner as to transmit the first fraction of each of the measurement and reference beams to said first detector means through the inlet and outlet sections of the measurement cell; and the second detector means is placed in such a manner as to receive the second fraction of the measurement and reference beams directly, the beam splitter being arranged in such a manner as to receive the reference beam after it has passed through the outlet section of the filter cell.

In another embodiment, the measurement cell containing the mixture of gases to be analyzed comprises an inlet section and an outlet section through which the entire measurement beam passes in succession; the beam splitter is placed in such a manner as to transmit the first fraction of each of the measurement and reference beams directly to said first detector means; and the second detector means is placed in such a manner as to receive the second fractions of the measurement and reference beams via the inlet and outlet sections of the filter cell, the beam splitter being arranged in such a manner as to receive the measurement beam after it has passed through the outlet section of the measurement cell.

The apparatus of the invention further comprises means for measuring the temperature of the medium in which the component elements of the apparatus are placed, and the signals delivered by said temperature measuring means are applied to said signal processing means for determining the absolute concentration of the gas to be detected.

The first and second emitter means can comprise light emitting diodes or laser diodes or solid lasers.

Modulator and filter means are associated with the emitter means. The modulation means are synchronized in such a manner that the first and second emitter means emit radiation in turns. The inlet and outlet sections of the measurement cell can be situated on the same side of the measurement cell or they can be on opposite sides.

The first and second emitter means can have emission spectra that are similar or different.

The invention also provides a method of detecting a gas by selective absorption of electromagnetic radiation to detect the presence of a particular gas within a mixture of gases, the method comprising the following steps:

a) emitting a measurement infrared electromagnetic radiation beam in a wavelength band containing a wavelength at which the gas to be detected presents an absorption characteristic;

b) emitting a reference infrared electromagnetic radiation beam;

c) modulating the emission of the measurement and reference beams in synchronized manner such that pulses of the measurement beam alternate in time with pulses of the reference beam;

d) causing at least a fraction of the measurement beam to pass through a measurement cell containing the mixture of gases;

e) causing at least a fraction of the reference beam to pass through a filter cell containing a sample of the gas to be detected;

f) separating the reference beam and the measurement beam into first and second fractions;

g) measuring the energies of the first fractions;

h) measuring the energies of the second fractions of the measurement and reference beams; and i) determining the absolute concentration of the gas to be detected by using the four signals ($U_S^1$, $U_S^2$, $U_R^1$, $U_2^R$) a representing the energy measured in the first and second fractions of the measurement and reference beams as delivered in succession when the pulses of the measurement and reference beams are emitted respectively, using the ratio $R=(U_S^1 \times U_R^2)/(U_S^2 \times U_R^1)$ between said four signals in which $U_S^1$ and $U_S^2$ respectively represent the energy measurement signals of the first and second fractions of the measurement and reference beams when the pulses of the measurement beam are emitted, and $U_R^1$ and $U_R^2$ respectively represent the energy measurement signals of the first and second fractions of the measurement and reference beams when the pulses of the reference beam are emitted.

The temperature of the medium in which the measurement and reference beams propagate is measured and the value determined for the absolute concentration of the gas to be detected is corrected as a function of the measured temperature.

In a particular implementation, the entire reference beam is passed through the filter cell containing a sample of the gas to be detected; said splitting is performed on the measurement beam and on the reference beam after it has passed through the filter cell; and the energies of the first fractions of the measurement and reference beams are measured after said first fractions have passed through the measurement cell containing the mixture of gases.

In another particular implementation the entire measurement beam is passed through the measurement cell containing the mixture of gases; said beam splitting is performed on the reference beam and on the measurement beam after it has passed through the measurement cell; and the energies of the second fractions of the measurement and reference beams are measured after these second fractions have passed through the filter cell containing a sample of the gas to be detected.

The method and the portable apparatus of the invention are particularly applicable to detecting methane, and sensitivity can be of the order of 1 ppm, for example, while selectivity can be very high when using infrared electromagnetic radiation.

Apparatuses of the invention can thus advantageously be used as a replacement for flame ionization appliances which suffer from the particular drawback of having no selectivity and of requiring gas cylinders containing a mixture of nitrogen and hydrogen in order to operate, whereas apparatuses of the invention require practically no maintenance. Furthermore, the absence of moving components or of components that require high energy consumption, such as electric motors, enables the invention to be used for making portable detectors that are compact, robust, and self-contained.

BRIEF DESCRIPTION OF THE DRAWINGS

Other characteristics and advantages of the invention will appear on reading the following description of particular embodiments given as examples and with reference to the accompanying drawings, in which.

MORE DETAILED DESCRIPTION

Figure 1:
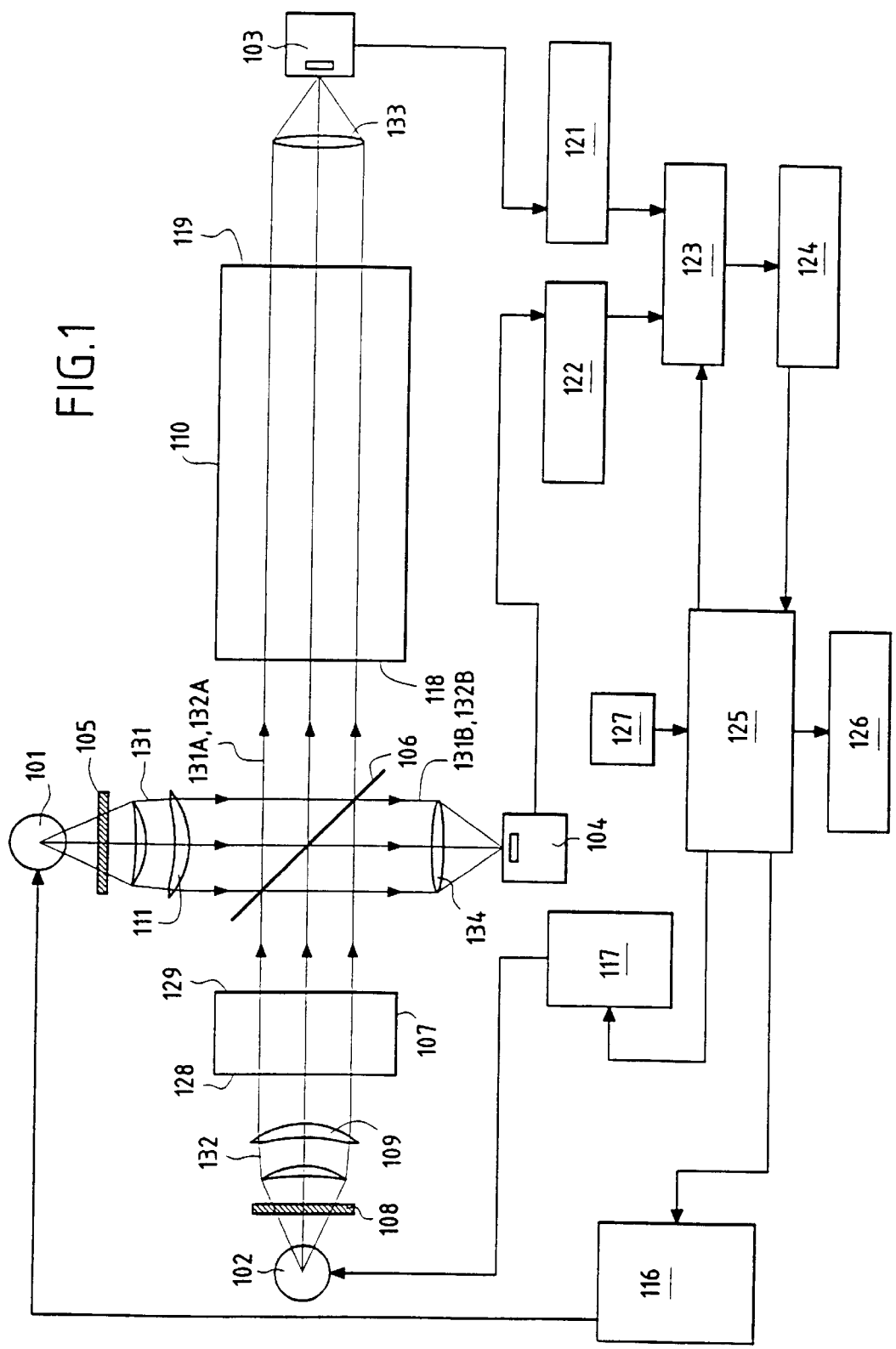
FIG. 1 is a diagrammatic view of a first embodiment of a gas detector of the present invention.

With reference initially to FIG. 1, there can be seen the optical system of a first embodiment of a gas detector of the invention for detecting and measuring the concentration of a predetermined gas present in a mixture of gases containing a plurality of gases having optical absorption spectra that overlap.

A first radiation source 101, such as a light emitting diode (LED) delivers a measurement beam 131 which passes through a narrow-band bandpass filter 105 covering a spectrum range containing absorption lines of the gas to be measured. The beam 131 then passes through a lens 111 so as to collimate the beam onto a beam splitter 106.

A second radiation source 102, such as an LED, supplies a reference beam 132 which passes through a narrow-band bandpass filter 108 covering a spectrum range containing absorption lines of the gas to be measured. The beam 132 then passes through a lens 109 so as to be collimated onto a filter cell 107 containing the gas to be detected.

The filter cell 107 or gas correlation cell contains the predetermined gas to be detected at high concentration, and it constitutes an optical gas filter providing a signature that corresponds to the absorption spectrum of the gas that is to be detected. The beam 132 reaches a front face of transparent material of the filter cell 107, which front face constitutes an inlet window 128, and it leaves via an opposite face of the filter cell 107, likewise made of transparent material, which opposite face constitutes an outlet window 129.

After passing through the lens 111, the beam 131 meets a beam splitter 106 that can be constituted by a single semi-transparent plate which reflects a fraction 131A of the measurement beam 131 and transmits a fraction 131B of the same beam.

After passing through the outlet face 129 of the filter cell 107, the beam 132 encounters the beam splitter 106 which transmits a fraction 132A of the reference beam 132 and which reflects a fraction 132B of the same beam.

The beams 131A and 132A are applied via an inlet section 118 to a measurement cell 110 adapted to contain the gas mixture to be analyzed. The beams 131A and 132A leave the measurement cell 110 through an outlet section 119 leading to a focusing lens 133 so as to cause them to converge on a first photodetector 103.

The beams 131B and 132B are transmitted through a focusing lens 134 so as to converge on a second photodetector 104.

The radiation sources 101 and 102 are associated with synchronized modulator means 116 and 117 so as to deliver pulsed light beams 131 and 132 in turns.

The apparatus of FIG. 1 gives rise to four output signals from the photodetectors 103 and 104.

A pulse from the source 101 (measurement beam 131) gives an output signal $U_S^1$ on the photodetector 103 and an output signal $U_S^2$ on the photodetector 104.

A pulse from the source 102 (reference beam 132) gives an output signal $U_R^1$ on the photodetector 103 and an output signal $U_R^2$ on the photodetector 104.

If the measurement cell 110 contains a gas mixture including the gas to be detected, then the signals $U_S^1$, $U_S^2$, $U_R^1$ and $U_R^2$ correspond respectively to the signals shown in FIGS. 6D, 6B, 6C, and 6A.

Using gas filter correlation techniques, the gas concentration as detected can be determined by the ratio $U_S^1/U_R^1$, i.e. by the ratio between the output signals from the photodetector 103.

Nevertheless, this ratio $U_S^1/U_R^1$ can vary not only because of the presence of the gas to be detected within the measurement cell 110, but also because of other undesirable factors such as the influence of temperature or the sources 101 and 102 degrading.

It is to avoid these drawbacks that the second photodetector 104 is included in the optical system in such a manner that the measurement beam 103 and the reference beam 132 strike the photodetector 104 without passing through the measurement cell 110.

In this case, the signals $U_S^2$ and $U_R^2$ do not depend on the concentration of the gas to be measured.

The ratio $R=(U_S^1 \times U_R^2)/(U_S^2 \times U_R^1)$ is independent of the sensitivity of the photodetectors and of the intensity of the sources. It can be represented as being the product of two ratios $R_1 \times R_2 = (U_S^1/U_R^1) \times (U_R^2/U_S^2)$. Each of these ratios $R_1, R_2$ represents a signal coming from a single photodetector; the ratios $R_1, R_2$ are therefore independent of the sensitivity of the photodetectors. The ratio R can also be represented as the product of two other ratios $R_S \times R_R = (U_S^1/U_S^2) \times (U_R^2/U_R^1)$. The signals of each of these ratios $R_S, R_R$ are produced by the same light source; the ratios $R_S, R_R$ are thus independent of the intensities of the light sources.

References 116 and 117 designate electrical power supply circuits for the radiation sources 101 and 102. The circuits 116 and 117 include synchronized pulse generators such that the LEDs 101 and 102 deliver pulsed light beams in alternation.

The means 121 to 126 are provided to perform the synchronous acquisition and processing of the four signals that are delivered successively by the detector means 103 and 104 when the light emitter means 101 and 102 are activated in succession, and they serve to determine the absolute concentration of the gas to be detected.

The photodetectors 103 and 104 deliver electrical signals that are proportional to the light intensity they receive. These signals are applied to amplifiers 121 and 122 whose outputs are connected to a multiplexer 123 in turn connected via an analog-to-digital connector 124 to a microprocessor 125 which synchronizes the modulators 116, 117 with the multiplexer 123. The microprocessor 125 also computes the concentration of the gas to be measured while also taking account of the temperature value supplied by a temperature detector 127 which can be constituted by a thermistor, for example. This temperature measurement could equally well be performed by measuring the dark resistance of one of the photodetectors 103, 104. The computed concentration value can be displayed on the screen 126.

The temperature compensation algorithm is described in detail in French patent document FR-A-2 772 127 entitled: [in translation] "A method of determining the concentration of a gas in a mixture of gases, and analysis apparatus for implementing such a method".

Nevertheless, the principle of such a temperature compensation algorithm suitable for use in the context of the present invention is described below by way of example.

This measurement principle relies on a calibration stage which serves to draw up two temperature compensation tables and one correspondence table between the measured signal and concentration. These three tables are then stored in the device and enable concentration to be measured under all temperature conditions corresponding to the calibration range.

The calibration stage comprises the following steps:

The signal $U^*_0(t)$ is recorded as measured by the device at zero concentration and as a function of temperature t:

TABLE a

| $U^*_0(t)$ |
|---|

The signal $U_{N_0}(t)$ is measured at a fixed concentration $N_0$ of the gas to be measured as a function of temperature t. Thereafter, the normalized transmittance $T^*_{N_0}(t)$ as defined below is recorded:

TABLE b

| $T^*_{N_0}(t) = \dfrac{U_{N_0}(t)}{U^*_0(t)}$ |
|---|

Finally, the signal $U_{t_0}(N)$ is measured as a function of the concentration of the gas to be measured at a fixed temperature $t_0$. Thereafter normalized transmittance is measured defined as follows:

TABLE c

| $T^*_{t_0}(N) = \dfrac{U_{t_0}(N)}{U_{t_0}(0)}$ |
|---|

Measuring concentration comprises the following steps:

The device measures the signal $U(N,t)$ and the temperature t.

Thereafter, normalized transmittance is calculated using Table a:

$$T(N, t) = \frac{U(N, t)}{U^*_0(t)} \quad (1)$$

This normalized transmittance value is then reduced to the temperature $t_0$ (at which concentration calibration was performed) by using the temperature compensation formula given in patent document FR-A-2 772 127 and Table b:

$$T(N, t_0) = T(N, t)\frac{\ln(T^*_{N_0}(t_0))}{\ln(T^*_{N_0}(t))} \quad (2)$$

or its simplified version as obtained by a limited development of the preceding formula:

$$T(N, t_0) = 1 - (1 - T(N, t))\frac{1 - T^*_{N_0}(t_0)}{1 - T^*_{N_0}(t)} \quad (3)$$

Thereafter, the measured concentration is determined using Table c which associates concentration N and normalized transmittance T at temperature $t_0$.

Figure 2:
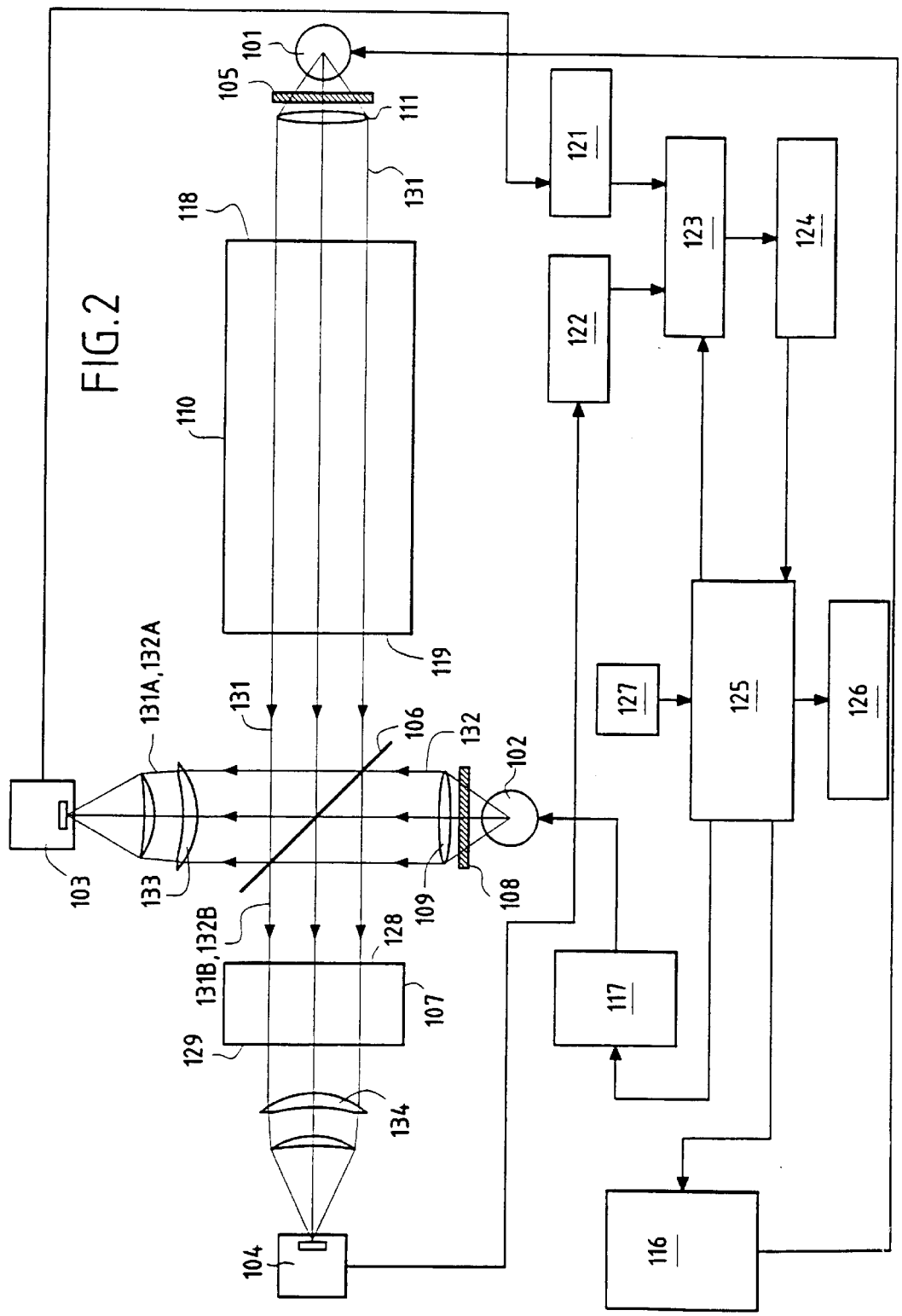
FIG. 2 is a diagrammatic view of a second embodiment of a gas detector of the present invention.
Figure 3:
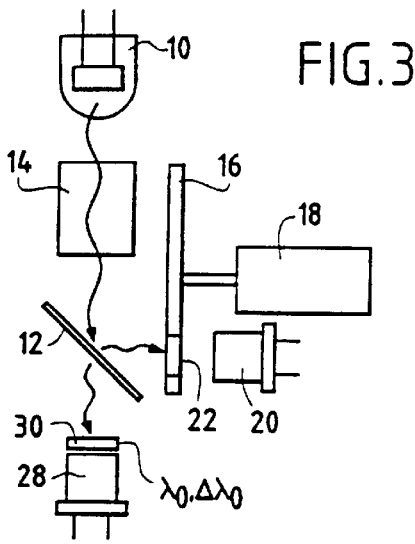
FIG. 3 is a diagrammatic view of a first prior art gas analyzer.
Figure 3A:
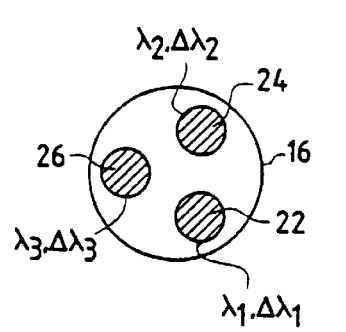
FIG. 3A is a detail view of the FIG. 3 gas analyzer.
Figure 4:
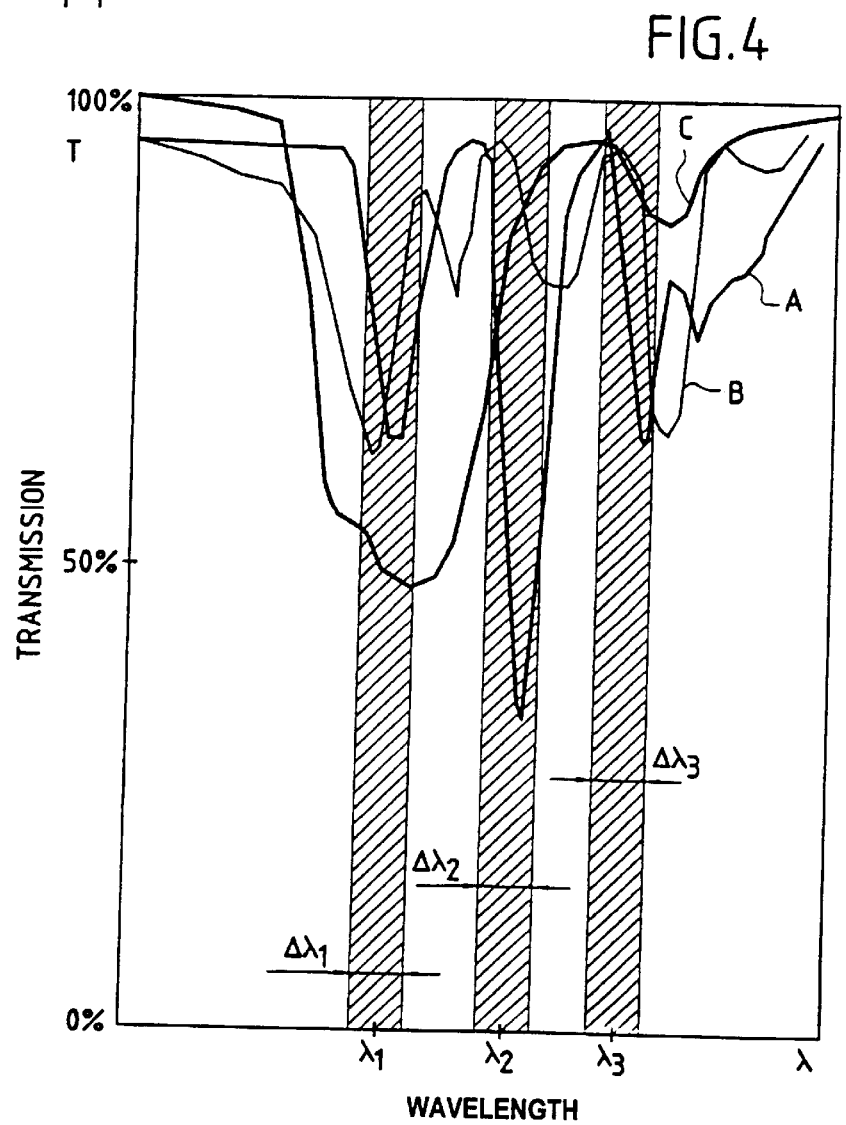
FIG. 4 is a spectrum diagram showing transmission as a function of wavelength for three gases analyzed using the gas analyzer of FIGS. 3 and 3A.
Figure 5:
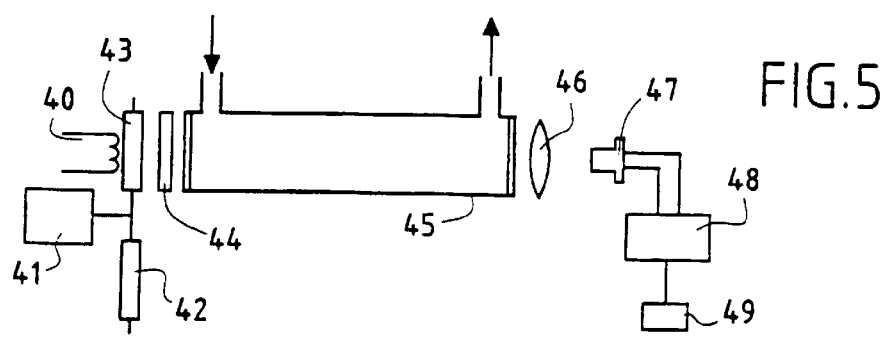
FIG. 5 is a diagram of a second prior art gas analyzer.
Figure 6A:
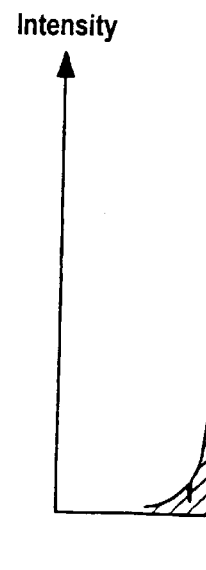
FIGS. 6A to 6D are a set of spectrum diagrams showing light intensity as a function of wavelength under various operating circumstances for the FIG. 5 gas analyzer.
Figure 6B:
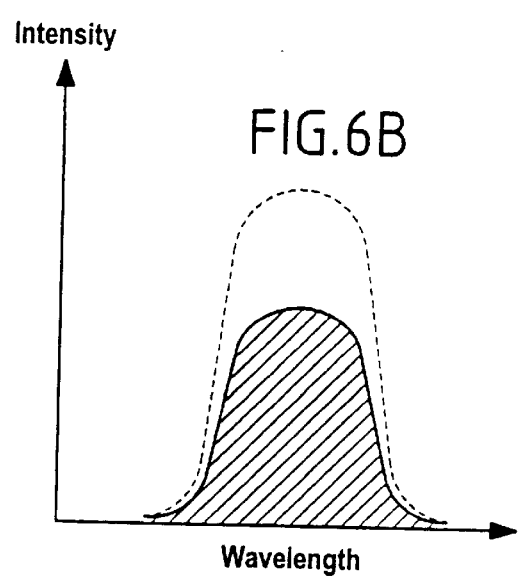
Figure 6C:
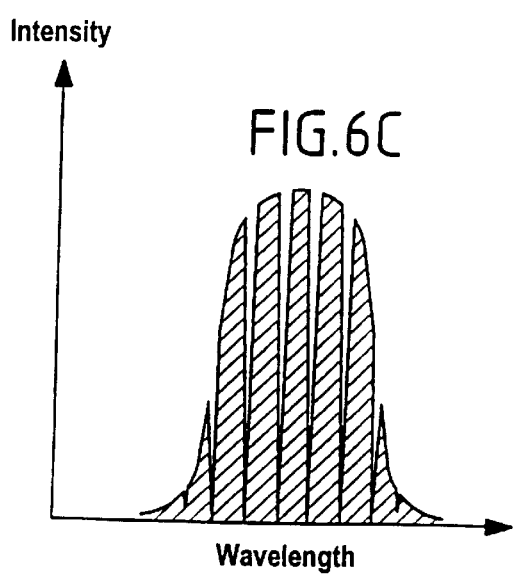
Figure 6D:
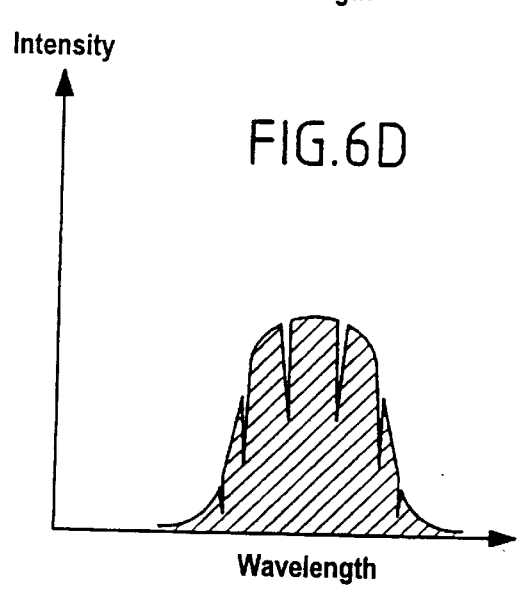

FIG. 2 shows another embodiment of a gas detector of the invention in the form of a block diagram showing the essential functions of the electronic processor circuits which are associated with the optical detector system. It should be observed that the changeover from FIG. 1 to FIG. 2 is obtained by swapping the positions of the measurement cell 110 and the reference cell 107.

In FIG. 2, elements that correspond to those shown in FIG. 1 are given the same reference numerals and they are not described again in detail.

The variant shown in FIG. 2 has a measurement beam 131 emitted by the radiation source 101 passing through a narrow-band bandpass filter 105 covering the spectrum range in which there are to be found absorption lines of the gas to be measured.

The measurement beam 131 is applied via the inlet section 118 to the measurement cell 110. The measurement beam 131 leaves the measurement cell 110 through the outlet section 119.

The beam 131 is collimated in the vicinity of the inlet section 118 by means of a lens 111. After passing through the outlet section 119, the beam 131 reaches the beam splitter 106 which reflects a fraction 131A on the measurement beam 131 to the first photodetector 103; it transmits a fraction 131B of the measurement beam 131 through the reference cell 107 after which it converges via a lens 134 onto a second photodetector 104.

The reference cell 107 or gas correlation cell contains the predetermined gas to be detected, at high concentration, and constitutes an optical filter whose signature corresponds to the absorption spectrum of the gas to be detected.

The portion 131B of the beam 131 reaches the inlet window 128 and leaves via the outlet window 129 of the reference cell 107.

The second radiation source 102 emits a reference beam 132 which strikes the beam splitter 106 directly, without passing through the measurement cell 110, and it is split in the beam splitter 106 into a first fraction 132A which passes through the splitter 106 so as to be converged by the lens 133 on the first photodetector 103, and a second fraction 132B which is reflected by the splitter 106 so as to converge via the lens 134 on the second photodetector 104 after passing through the filter cell 107 like the second fraction 131B of the measurement beam 131.

The signals received by each of the photodetectors 103 and 104 are analogous to those received by the same photodetectors in the apparatus of FIG. 1. The processing applied to these signals is likewise similar to that applied by the FIG. 1 apparatus and as described above.

Furthermore, a temperature sensor 127 is placed in the vicinity of the elements constituting the detector apparatus, outside the measurement cell 110. When computing the concentration of a gas by optical absorption measurements, it is necessary to take account of the temperature of the gas to be analyzed because its spectrum depends on temperature.

The embodiments described with reference to FIGS. 1 and 2 can be varied in numerous ways. In particular, the measurement cell 110 within which interaction occurs between light and the gas medium to be analyzed can present a variety of light beam paths depending on the application. In a variant, using an even number of light beam paths, the inlet and outlet sections of each measurement cell 110 can be situated on the same side of the measurement cell 110.

The measurement cell 110 can constitute a closed enclosure having inlets and outlets for the gas medium to be analyzed. The measurement cell 110 can also constitute an open cell which is in communication with the outside environment, but is nevertheless separated from the portion which incorporates the radiation sources 101, 102, the photodetectors 103, 104, the gas correlation cell 107, and the electronic processing circuits.

The light emitting sources 101 and 102, which must necessarily cover wavelengths including spectrum lines of the gas to be detected, can emit anywhere in the optical spectrum, including in the infrared and in the ultraviolet.

For a gas such as methane, the absorption wavelengths lie in the infrared. The sources 101 and 102 are therefore sources for emitting infrared radiation when the detector is for detecting methane leaks. Such emitter sources 101 and 102 can be constituted by black bodies (filament lamps), LEDs, or indeed by lasers (laser diodes or solid lasers). Laser diodes provide a good quality to price ratio, making it possible to detect small gas leaks selectively at reasonable cost.

Methane has a spectrum with numerous very fine absorption lines and is therefore well adapted to the measurement method of the invention in which broadband light emitters 101 and 102 are used and in which the gas correlation cell 107 is filled with 100% by volume of methane, thereby constituting an optical filter whose signature corresponds to the methane absorption spectrum, thereby enabling methane to be distinguished from other gases. Insofar as there is no complete overlap between the methane spectrum and the spectrum of the other gases, the method presents very good selectivity.

The measurement signals are processed in the present invention by multiplying two ratios of two signals each, and it does not rely on a difference between two signals, thus making it pointless to use a compensating filter and indeed to regulate the second source of electromagnetic radiation, which is particularly important in the context of a device that is to be compact, portable, and suitable of use in explosive atmospheres, given that its consumption of electricity can be very low.

In the particular case of an application for detecting methane, it is advantageous to make use of a fraction only of the methane absorption band around 3.2 micrometers in order to minimize other interfering elements, such as other alkanes, for example. Using only a fraction of the absorption band instead of the entire absorption band of the gas to be measured serves to increase selectivity.

Under such circumstances, it is possible to use infrared LEDs having their spectrum optimized around 3.2 micrometers, thus requiring consumption that is very low, not exceeding a few tens of milliwatts.

What is claimed is:

1. Portable apparatus for detecting gas by selective absorption of electromagnetic radiation to detect the presence of a particular gas in a gas mixture, the apparatus comprising:
   a) first emitter means for emitting a measurement infrared electromagnetic radiation beam in a wavelength band containing a wavelength at which the gas to be detected presents an absorption characteristic;
   b) second emitter means for emitting a reference infrared electromagnetic radiation beam, said first and second emitter means being activated in alternation;
   c) a measurement cell containing the gas mixture to be analyzed, which measurement cell has an inlet section and an outlet section and receives at least a fraction of the measurement beam through its inlet section;
   d) a filter cell containing a sample of the gas to be detected and having an inlet section and an outlet section, through which sections at least a fraction of the reference beam passes in succession;
   e) first detector means for detecting electromagnetic radiation beams;
   f) second detector means for detecting electromagnetic radiation beams;
   g) a beam splitter disposed in such a manner as to split firstly the measurement beam and secondly the reference beam so as to transmit a first fraction of each of the measurement and reference beams to said first detector means, and a second fraction of each of the measurement and reference beams to the second detector means; and
   h) processing and acquisition means for synchronously acquiring and processing the four signals $U_S^1$, $U_S^2$, $U_R^1$, $U_R^2$ delivered by the first and second detector means in succession when the first and second emitter means are respectively activated in order to determine the absolute concentration of the gas to be detected on the basis of the ratio $R=(U_S^1 \times U_R^2)/(U_S^2 \times U_R^1)$ between said four signals where $U_S^1$ and $U_S^2$ respectively represent the signals delivered by the first and second detector means when the first emitter means is activated, and where $U_R^1$ and $U_R^2$ respectively represent the signals delivered by the first and second detector means when the second emitter means is activated.

2. The apparatus of claim 1, wherein the filter cell containing a sample of gas to be detected has inlet and outlet sections through which the entire reference beam passes in succession, wherein the beam splitter is placed in such a manner as to transmit the first fraction of each of the measurement and reference beams to said first detector means through the inlet and outlet sections of the measurement cell, and wherein the second detector means is placed in such a manner as to receive the second fraction of the measurement and reference beams directly, the beam splitter being arranged in such a manner as to receive the reference beam after it has passed through the outlet section of the filter cell.

3. Apparatus of claim 1, wherein the measurement cell containing the mixture of gases to be analyzed comprises an inlet section and an outlet section through which the entire measurement beam passes in succession, wherein the beam splitter is placed in such a manner as to transmit the first fraction of each of the measurement and reference beams directly to said first detector means, and wherein the second detector means is placed in such a manner as to receive the second fractions of the measurement and reference beams via the inlet and outlet sections of the filter cell, the beam splitter being arranged in such a manner as to receive the measurement beam after it has passed through the outlet section of the measurement cell.

4. Apparatus according to claim 1, further comprising means for measuring the temperature of the medium in which the component elements of the apparatus are placed, and wherein the signals delivered by said temperature measuring means are applied to said processing means.

5. Apparatus according to claim 1, wherein the first and second emitter means comprise light emitting diodes.

6. Apparatus according to claim 1, wherein the first and second emitter means comprise laser diodes or solid lasers.

7. Apparatus according to claim 1, including modulator means associated with the emitter means, which modulator means are synchronized in such a manner that the first and second emitter means emit radiation in turns.

8. Apparatus according to claim 1, including filter means associated with the emitter means.

9. Apparatus according to claim 1, wherein the beam splitter comprises a semitransparent plate for transmitting a fraction of the electromagnetic radiation, and for reflecting a fraction thereof.

10. Apparatus according to claim 1, wherein the inlet and outlet sections of the measurement cell are situated on the same side of said measurement cell.

11. Apparatus according to claim 1, wherein the inlet and outlet sections of the measurement cell are situated on opposite sides of said measurement cell.

12. Apparatus according to claim 1, wherein the inlet and outlet sections of the filter cell are situated on opposite faces of the filter cell.

13. Apparatus according to claim 1, wherein the gas to be detected is methane.

14. Apparatus according to claim 1, wherein the first and second emitter means for emitting electromagnetic radiation beams present similar emission spectra.

15. Apparatus according to claim 1, wherein the first and second emitter means for emitting electromagnetic radiation beams present different emission spectra.

16. A method of detecting a gas by selective absorption of electromagnetic radiation to detect the presence of a particular gas within a mixture of gases, the method comprising the following steps:

a) emitting a measurement infrared electromagnetic radiation beam in a wavelength band containing a wavelength at which the gas to be detected presents an absorption characteristic;

b) emitting a reference infrared electromagnetic radiation beam;

c) modulating the emission of the measurement and reference beams in synchronized manner such that pulses of the measurement beam alternate in time with pulses of the reference beam;

d) causing at least a fraction of the measurement beam to pass through a measurement cell containing the mixture of gases;

e) causing at least a fraction of the reference beam to pass through a filter cell containing a sample of the gas to be detected;

f) separating the reference beam and the measurement beam into first and second fractions;

g) measuring the energies of the first fractions of the measurement and reference beams;

h) measuring the energies of the second fractions of the measurement and reference beams; and i) determining the absolute concentration of the gas to be detected by using the four signals $U_S^1$, $U_S^2$, $U_R^1$, $U_R^2$ representing the energy measured in the first and second fractions of the measurement and reference beams as delivered in succession when the pulses of the measurement and reference beams are emitted respectively, using the ratio $R=(U_S^1 \times U_R^2)/(U_S^2 \times U_R^1)$ between said four signals in which $U_S^1$ and $U_S^2$ respectively represent the energy measurement signals of the first and second fractions of the measurement and reference beams when the pulses of the measurement beam are emitted, and $U_R^1$ and $U_R^2$ respectively represent the energy measurement signals of the first and second fractions of the measurement and reference beams when the pulses of the reference beam are emitted.

17. A method according to claim 16, wherein the temperature of the medium in which the measurement and reference beams propagate is measured and the value determined for the absolute concentration of the gas to be detected is corrected as a function of the measured temperature.

18. A method according to claim 16, wherein the gas to be detected is methane.

19. A method according to claim 16, wherein the entire reference beam is passed through the filter cell containing a sample of the gas to be detected, wherein said splitting is performed on the measurement beam and on the reference beam after it has passed through the filter cell, and wherein the energies of the first fractions of the measurement and reference beams are measured after said first fractions have passed through the measurement cell containing the mixture of gases.

20. A method according to claim 16, wherein the entire measurement beam is passed through the measurement cell containing the mixture of gases, wherein said beam splitting is performed on the reference beam and on the measurement beam after it has passed through the measurement cell, and wherein the energies of the second fractions of the measurement and reference beams are measured after these second fractions have passed through the filter cell containing a sample of the gas to be detected.

* * * * *